(12) United States Patent
Aoyama

(10) Patent No.: US 11,089,949 B2
(45) Date of Patent: Aug. 17, 2021

(54) ENDOSCOPE SYSTEM AND METHOD OF OPERATING SAME

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 16/283,844

(22) Filed: Feb. 25, 2019

(65) Prior Publication Data

US 2019/0183319 A1 Jun. 20, 2019

Related U.S. Application Data

(63) Continuation of application No. PCT/JP2017/024894, filed on Jul. 7, 2017.

(30) Foreign Application Priority Data

Sep. 30, 2016 (JP) .............................. JP2016-193133

(51) Int. Cl.
*A61B 1/00* (2006.01)
*A61B 1/04* (2006.01)
(Continued)

(52) U.S. Cl.
CPC ...... *A61B 1/00188* (2013.01); *A61B 1/00006* (2013.01); *A61B 1/00009* (2013.01); (Continued)

(58) Field of Classification Search
CPC ............ A61B 1/00188; A61B 1/00006; A61B 1/00009; A61B 1/00045; A61B 1/043; A61B 1/0638; G02B 23/2469
See application file for complete search history.

(56) References Cited

U.S. PATENT DOCUMENTS

| 4,488,039 A | 12/1984 | Sato et al. |
| 5,817,014 A | 10/1998 | Hori et al. |

(Continued)

FOREIGN PATENT DOCUMENTS

| JP | 2009022376 | 2/2009 |
| JP | 2012110481 | 6/2012 |

(Continued)

OTHER PUBLICATIONS

"International Search Report (Form PCT/ISA/210) of PCT/JP2017/024894," dated Sep. 26, 2017, with English translation thereof, pp. 1-3.

(Continued)

*Primary Examiner* — Timothy J Neal
*Assistant Examiner* — William B Chou
(74) *Attorney, Agent, or Firm* — JCIPRNET

(57) ABSTRACT

Provided are an endoscope system and a method of operating the same capable of reliably performing focusing even in a case where an observation target is illuminated with light including long-wave light. A movable lens moves in an optical axis direction. A lens drive unit moves the movable lens from a first lens position of the movable lens where an observation target illuminated with short-wave light is focused to a second lens position of the movable lens where the observation target illuminated with long-wave light having a longer wavelength than the short-wave light is focused.

20 Claims, 11 Drawing Sheets

| FIRST MAGNIFICATION | SECOND MAGNIFICATION FOR NORMAL LIGHT | SECOND MAGNIFICATION FOR SPECIAL LIGHT |
|---|---|---|
| 1.1 TIMES | 1.15 TIMES | 1.18 TIMES |
| 10 TIMES | 11 TIMES | 12 TIMES |

(51) Int. Cl.
*A61B 1/06* (2006.01)
*G02B 23/24* (2006.01)

(52) U.S. Cl.
CPC ........ *A61B 1/00045* (2013.01); *A61B 1/043* (2013.01); *A61B 1/0638* (2013.01); *G02B 23/2469* (2013.01)

(56) References Cited

U.S. PATENT DOCUMENTS

| | | | | |
|---|---|---|---|---|
| 7,181,265 | B2* | 2/2007 | Sendai | A61B 5/0071 600/473 |
| 8,488,903 | B2* | 7/2013 | Higuchi | G06T 5/50 382/274 |
| 8,711,252 | B2* | 4/2014 | On | G06T 7/231 348/241 |
| 9,621,781 | B2* | 4/2017 | On | A61B 1/045 |
| 2011/0237894 | A1* | 9/2011 | Ozawa | A61B 1/043 600/168 |
| 2016/0295085 | A1* | 10/2016 | Aoyama | A61B 1/00009 |
| 2017/0360275 | A1* | 12/2017 | Yoshizaki | A61B 1/0653 |
| 2018/0146844 | A1* | 5/2018 | Okazaki | A61B 1/00009 |

FOREIGN PATENT DOCUMENTS

| | | |
|---|---|---|
| JP | 2012213439 | 11/2012 |
| JP | 2014014716 | 1/2014 |

OTHER PUBLICATIONS

"Written Opinion of the International Searching Authority (Form PCT/ISA/237) of PCT/JP2017/024894," dated Sep. 26, 2017, with English translation thereof, pp. 1-13.
"Search Report of Europe Counterpart Application", dated Aug. 8, 2019, pp. 1-8.
Office Action of Japan Counterpart Application, with English translation thereof, dated Jun. 4, 2019, pp. 1-6.

* cited by examiner

| FIRST MAGNIFICATION | SECOND MAGNIFICATION FOR NORMAL LIGHT | SECOND MAGNIFICATION FOR SPECIAL LIGHT |
|---|---|---|
| 1.1 TIMES | 1.15 TIMES | 1.18 TIMES |
| | | |
| 10 TIMES | 11 TIMES | 12 TIMES |
| | | |

ENDOSCOPE SYSTEM AND METHOD OF OPERATING SAME

CROSS-REFERENCE TO RELATED APPLICATIONS

This application is a Continuation of PCT International Application No. PCT/JP2017/024894 filed on Jul. 7, 2017, which claims priority under 35 U.S.C § 119(a) to Japanese Patent Application No. 2016-193133 filed on Sep. 30, 2016. Each of the above application(s) is hereby expressly incorporated by reference, in its entirety, into the present application.

BACKGROUND OF THE INVENTION

1. Field of the Invention

The present invention relates to an endoscope system and a method of operating the same that performs focusing on an observation target.

2. Description of the Related Art

In the medical field, diagnosis using an endoscope system comprising a light source device, an endoscope, and a processor device has been performed widely. The endoscope system irradiates an observation target via the endoscope with illumination light from the light source device, and the processor device produces an image of the observation target on the basis of image signals obtained by capturing the observation target under illumination with the illumination light. By displaying the image on a monitor, a doctor can perform diagnosis while viewing this image on the monitor.

In a case where diagnosis is performed by a doctor, a distal end part of the endoscope provided with an imaging sensor is moved in a direction of insertion into the body, and is brought close to or separated from the observation target in accordance with a situation. As the distal end part of the endoscope moves in this way, a distance from the observation target may vary, the observation target may not be focused, and an image may not be easily seen. Additionally, also in a case where the observation target is magnified by a zoom lens, the observation target may not be focused. Against such a problem, JP2012-110481A discloses automatically focusing the observation target by adding an auto-focusing function to the endoscope.

SUMMARY OF THE INVENTION

In a case where the auto-focusing function is added to the endoscope as in JP2012-110481A, it is necessary to add a focus lens and a drive unit that drives the focus lens to the distal end part of the endoscope. For that reason, the addition of the auto-focusing function will hinder compacting of the endoscope distal end part. Hence, nowadays, it is general to finely adjust the position of the distal end part or to use the zoom lens to focus the observation target.

In a case where the focusing is performed using the zoom lens, the doctor checks whether or not the observation target on a monitor is focused by operating a zooming operating unit. However, in a case where the observation target is illuminated with broadband illumination light including long-wave light, such as red light, the illumination light reaches even a deep portion inside a tissue. Therefore, whether or not the observation target is focused on an image of the monitor may not be easily checked.

An object of the invention is to provide an endoscope system and a method of operating the same capable of reliably performing focusing even in a case where an observation target is illuminated with light including long-wave light in a case where focusing is performed using a zoom lens.

An endoscope system of the invention comprises a movable lens that moves in an optical axis direction; and a lens drive unit that moves the movable lens from a first lens position of the movable lens where an observation target illuminated with short-wave light is focused to a second lens position of the movable lens where the observation target illuminated with long-wave light having a longer wavelength than the short-wave light is focused.

It is preferable that in a case where the movable lens is a zoom lens that magnifies the observation target, the endoscope system has a magnification conversion table in which a first magnification in a case where the zoom lens is at the first lens position and a second magnification in a case where the zoom lens is at the second lens position are stored in association with each other; and a magnification conversion unit that converts the first magnification into the second magnification with reference to the magnification conversion table, and the lens drive unit moves the zoom lens to the second lens position by setting the zoom lens to have the second magnification. It is preferable that the endoscope system further comprises a position conversion table in which a relationship between the first lens position and the second lens position is stored; and a lens position calculation unit that calculates the second lens position from the first lens position with reference to the position conversion table.

It is preferable that the endoscope system further comprises a light source capable of independently emitting light of a plurality of colors including violet light, blue light, or red light, the short-wave light is the violet light or the blue light, the long-wave light is light including the red light among the light of the plurality of colors, and a first image obtained by imaging the observation target illuminated with the violet light or the blue light is displayed on a display unit. It is preferable that the endoscope system further comprises a light source control unit that performs a control for emitting the short-wave light on the light source, and performs a control for switching the short-wave light to the long-wave light on the light source after the movable lens is moved from the first lens position to the second lens position. It is preferable that the endoscope system further comprises a light source control unit that performs a control for emitting the short-wave light on the light source, and performs a control for switching the short-wave light to the long-wave light on the light source before the movable lens is moved from the first lens position to the second lens position.

It is preferable that the short-wave light is light having a spectrum that has a first peak in a short-wave range and has a skirt on a longer wavelength side than the short-wave range, and the long-wave light is light that has a second peak on a longer wavelength side than the first peak, and a first image obtained by imaging the observation target illuminated with the short-wave light is displayed on a display unit. It is preferable that the endoscope system further comprises a light source capable of independently emitting light of a plurality of colors, and the short-wave light or the long-wave wave is multicolor light obtained by combining the light of the plurality of colors together. It is preferable that the short-wave light or the long-wave light is broadband light including one or a plurality of short-wave narrowband light rays and fluorescence obtained by converting wavelengths of the short-wave narrowband light rays using a wavelength converting member.

It is preferable that the endoscope system further comprises a light source that emits broadband light having a wavelength range including the short-wave light and the long-wave light, an image acquisition unit that acquires a first image having wavelength information corresponding to the short-wave light among images, in a plurality of bands, having information of the observation target illuminated with the broadband light, and a display unit that displays the first image. It is preferable that the endoscope system further comprises a light source that sequentially emits the short-wave light and the long-wave light; an image acquisition unit that acquires a first image obtained by imaging the observation target illuminated with the short-wave light; and a display unit that displays the first image. It is preferable that the endoscope system further comprises an image acquisition unit that acquires a second image obtained by imaging the observation target illuminated with the long-wave light; and a display unit that displays the second image.

An endoscope system of the invention comprises a movable lens that moves in an optical axis direction; and a lens drive unit that moves the movable lens from a first lens position of the movable lens where an observation target illuminated with short-wave light is focused to a second lens position of the movable lens where the observation target illuminated with long-wave light having a longer wavelength than the short-wave light is focused. In a case where the movable lens is a zoom lens that magnifies the observation target, the endoscope system has a magnification conversion table in which a first magnification in a case where the zoom lens is at a first lens position and a second magnification in a case where the zoom lens is at a second lens position are stored in association with each other; and a magnification conversion unit that converts the first magnification into the second magnification with reference to the magnification conversion table. The lens drive unit moves the zoom lens to the second lens position by setting the zoom lens to have the second magnification.

The invention provides a method of operating an endoscope system having a movable lens that moves in an optical axis direction. The method comprises a step of moving the movable lens, using a lens drive unit, from a first lens position of the movable lens where an observation target illuminated with short-wave light is focused to a second lens position of the movable lens where the observation target illuminated with long-wave light having a longer wavelength than the short-wave light is focused.

Accordingly, it is possible to reliably perform focusing even in a case where an observation target is illuminated with light including long-wave light.

DESCRIPTION OF THE PREFERRED EMBODIMENTS

First Embodiment

Figure 1:
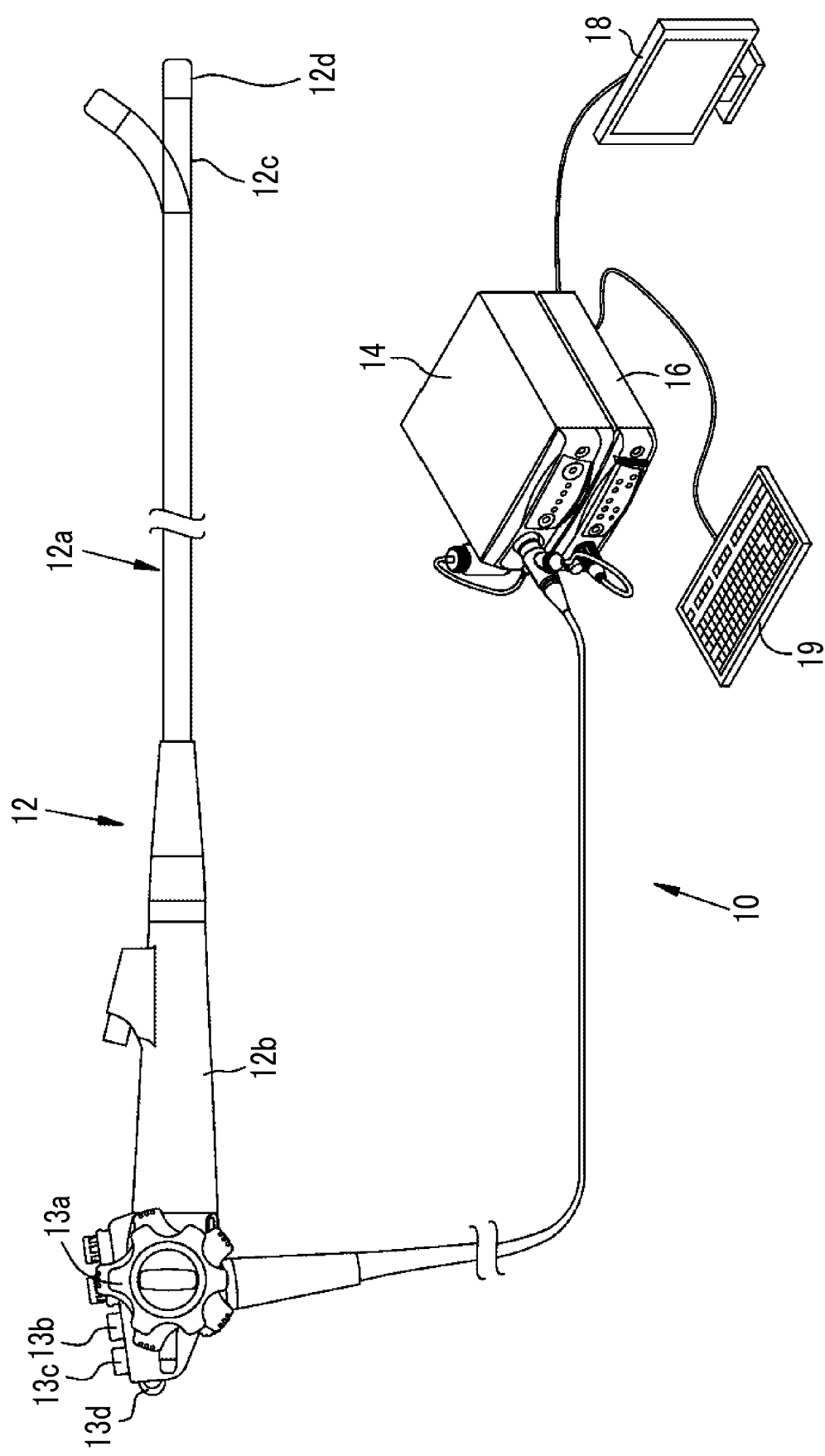
FIG. 1 is an external view of an endoscope system.

As illustrated in FIG. 1, an endoscope system 10 has an endoscope 12, a light source device 14, a processor device 16, a monitor 18 (display unit), and a console 19. The endoscope 12 is optically connected to the light source device 14, and is electrically connected to the processor device 16. The endoscope 12 has an insertion part 12a to be inserted into a subject, an operating part 12b provided at a proximal end portion of the insertion part 12a, and a bending part 12c and a distal end part 12d provided on a distal end side of the insertion part 12a. By operating an angle knob 13a of the operating part 12b, the bending part 12c makes a bending motion. The distal end part 12d is directed in a desired direction by this bending motion.

Additionally, the operating part 12b is provided with a still image acquisition unit 13b used for operating the acquisition of still images, a mode switching unit 13c used for operating the switching of observation modes, and a zooming operating unit 13d used for operating the change of a zoom magnification factor, in addition to the angle knob 13a. In the still image acquisition unit 13b, a freeze operation of displaying a still image of an observation target on the monitor 18, and a release operation of saving the still image in a storage are possible.

The endoscope system 10 has a normal mode and a special mode as the observation modes. In a case where an observation mode is the normal mode, the light source device 14 emits normal light obtained by combining light of a plurality of colors together in a quantity-of-light ratio Lc for normal mode, and displays a normal image on a monitor 18 on the basis of image signals obtained by imaging the observation target under illumination with this normal light. Additionally, in a case where an observation mode is the special mode, the light source device 14 emits special light obtained by combining a plurality of colors of light components together in a quantity-of-light ratio Ls for special mode, and displays a special image on the monitor 18 on the basis of image signals obtained by imaging the observation target under illumination with this special light.

The processor device 16 is electrically connected to the monitor 18 and the console 19. The monitor 18 outputs and displays an image of the observation target, information accompanying the image, and the like. The console 19 functions as a user interface that receives input operations, such as designation or the like of a region of interest (ROI) and function setting.

Figure 2:
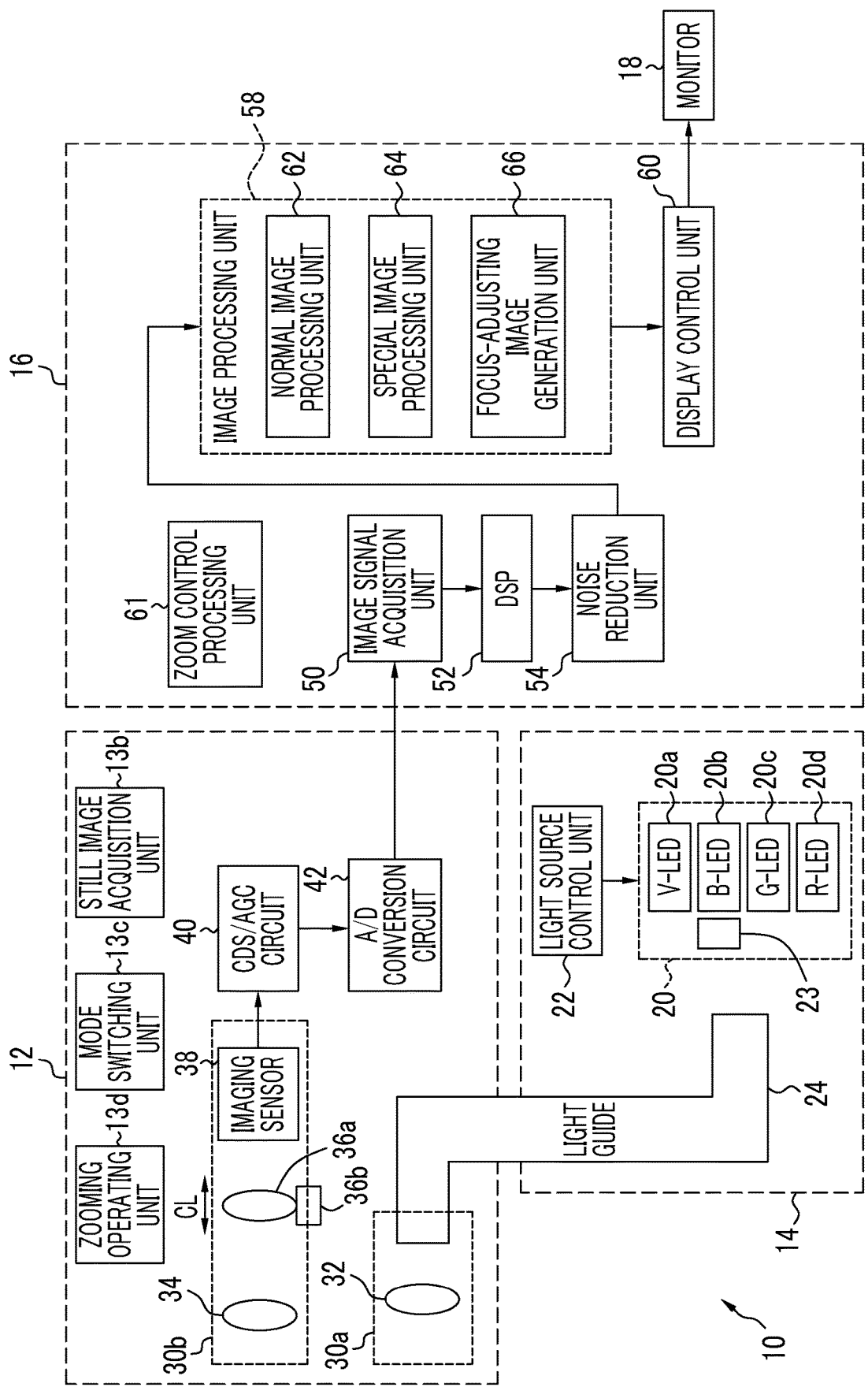
FIG. 2 is a block diagram illustrating the functions of the endoscope system of the first embodiment.

As illustrated in FIG. 2, the light source device 14 comprises a light source 20 that emits the illumination light to be used for illumination of the observation target, and a light source control unit 22 that controls the light source 20. The light source 20 is semiconductor light sources, such as a plurality of colors of light emitting diodes (LEDs). The light source control unit 22 controls the quantity of light emission of the illumination light by ON/OFF of the LEDs and the adjustment of the driving currents or driving voltages of the LEDs. Additionally, the light source control unit 22 controls the wavelength range of the illumination light, for example, by changing the optical filters.

Figure 3:
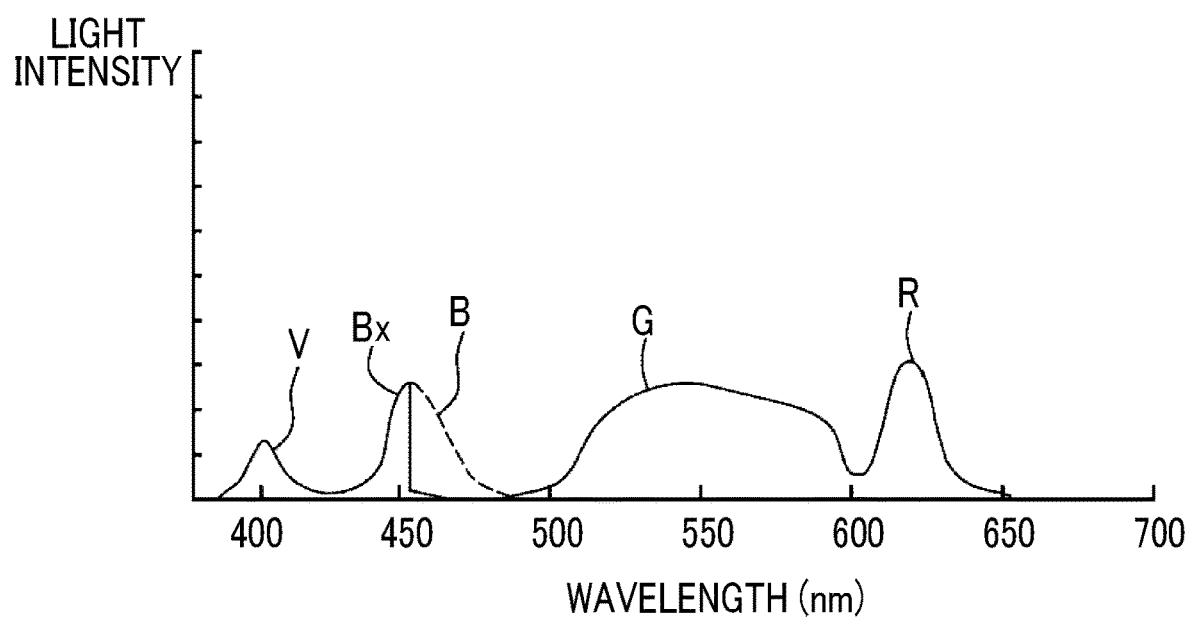
FIG. 3 is a graph illustrating the spectroscopic spectrum of violet light V, blue light B, blue light Bx, green light and red light R.

In the first embodiment, the light source 20 has four color LEDs of a violet light emitting diode (V-LED) 20a, a blue light emitting diode (B-LED) 20b, a green light emitting diode (G-LED) 20c, a red light emitting diode (R-LED) 20d, and a wavelength cutoff filter 23. As illustrated in FIG. 3, the V-LED 20a emits violet light V having a wavelength range of 380 nm to 420 nm.

The B-LED 20b emits blue light B having a wavelength range of 420 nm to 500 nm. The blue light B emitted from the B-LED 23b is cut by the wavelength cutoff filter 23 on at least a longer wavelength side than the peak wavelength 450 nm. Accordingly, the blue light Bx after being transmitted through the wavelength cutoff filter 23 has a wavelength range of 420 to 460 nm. In this way, the reason why light in a wavelength range on the longer wavelength side than 460 nm is cut is that the light in the wavelength range on the longer wavelength side than 460 nm is a factor in which the blood vessel contrast of blood vessels that is the observation target is lowered. In addition, the wavelength cutoff filter 23 may reduce the light in the wavelength range on the longer wavelength side than 460 nm instead of cutting the light in the wavelength range on the longer wavelength side than 460 nm.

The G-LED 20c emits green light G having a wavelength range of 480 nm to 600 nm. The R-LED 20d emits red light R having a wavelength range of 600 nm to 650 nm. In addition, center wavelengths and peak wavelengths of the respective colors of light emitted from the LEDs 20a to 20d may be the same as each other or may be different from each other.

The light source control unit 22 independently controls ON/OFF of the respective LEDs 20a to 20d, the quantity of light emission at the time of ON, and the like, thereby adjusting the light emission timing of illumination light, a light emission period, the quantity of light, and a spectroscopic spectrum. The control of ON and OFF in the light source control unit 22 varies in the respective observation modes.

Figure 4:
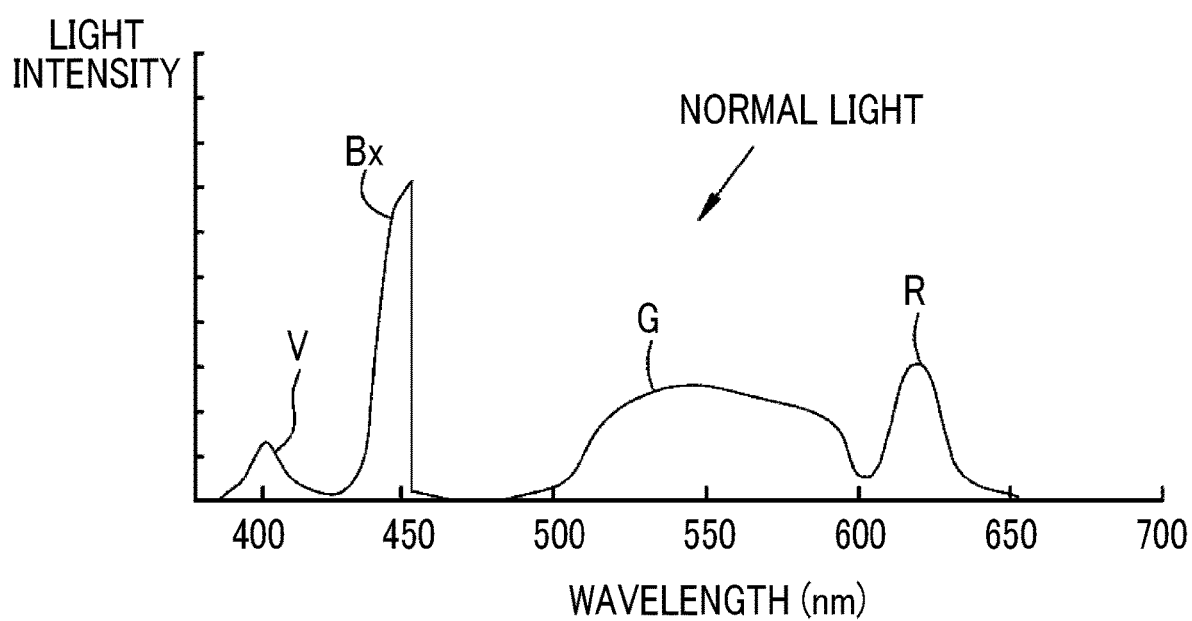
FIG. 4 is a graph illustrating the spectroscopic spectrum of normal light of the first embodiment.

In the case of the normal mode, the light source control unit 22 turns on the V-LED 20a, the B-LED 20b, the G-LED 20c, and the R-LED 20d altogether. In that case, as illustrated in FIG. 4, the quantity-of-light ratio Lc between the violet light V, the blue light B, the green light and the red light R is set such that the quantity of light emission of the blue light Bx becomes larger than the quantity of light emission of any of the violet light V, the green light and the red light R. Accordingly, in the normal mode, multicolor light for normal mode including the violet light V, the blue light Bx, the green light and the red light R is emitted as the normal light from the light source device 14. Since the normal light has an intensity equal to or more than a given level from a blue range to a red range, the normal light is substantially white.

Figure 5:
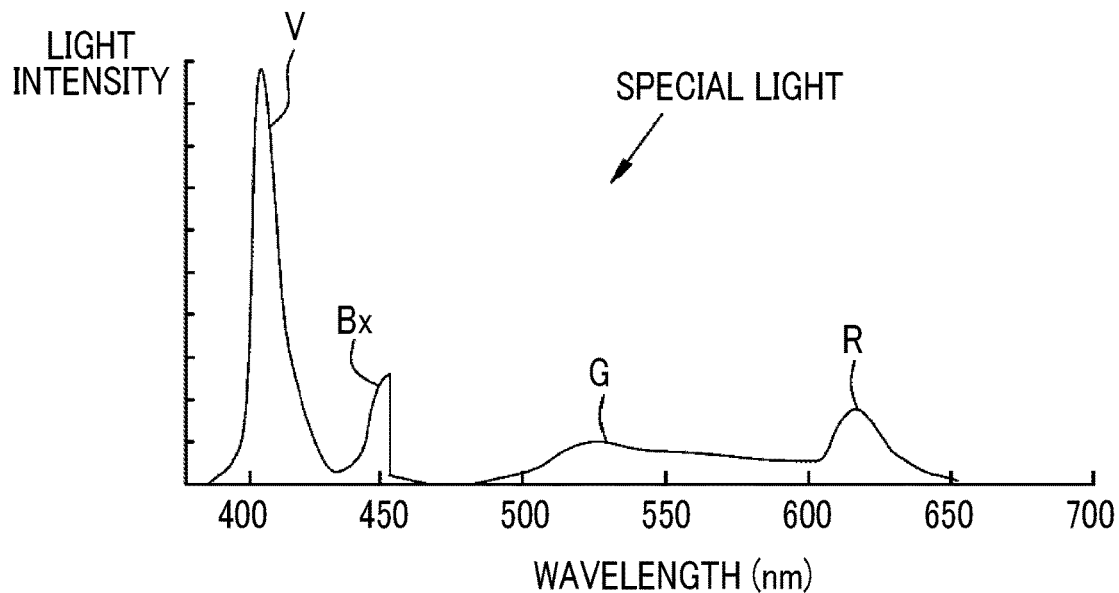
FIG. 5 is a graph illustrating the spectroscopic spectrum of special light of the first embodiment.

Even in the case of the special mode, the light source control unit 22 turns on the V-LED 20a, the B-LED 20b, the G-LED 20c, and the R-LED 20d altogether. In that case, as illustrated in FIG. 5, the quantity-of-light ratio Ls between the violet light V, the blue light B, the green light and the red light R is set such that the quantity of light emission of the violet light V becomes larger than the quantity of light emission of any of the blue light Bx, the green light and the red light R and such that the green light G and the red light R become smaller than the violet light V and the blue light Bx. Accordingly, in the special mode, multicolor light for special mode including the violet light V, the blue light Bx, the green light and the red light R is emitted as the special light from the light source device 14. Since the quantity of light emission of the violet light V is large, the special light is bluish light.

In addition, in a case where the spectra of the normal light and the special light are compared, respectively, the special light is light having a spectrum that has a peak (corresponding to "a first peak" of the invention) of light intensity, such as a peak of the violet light V, in a short-wave range, such as a blue range, and has a skirt in a longer wavelength side than the short-wave range, such as the green light G and the red light R. On the other hand, the normal light is light having a spectrum that has a peak (corresponding to "a second peak" of the invention) of the light intensity, such as a peak of the blue light Bx, in the short-wave range, such as the blue range, and has a peak on a longer wavelength side than the peak of the special light.

In any in the normal mode and the special mode, in a case where the zooming operating unit 13d is operated, the light source control unit 22 performs the control of turning off the B-LED 20b, the G-LED 20c, and the R-LED 20d and turning on only the V-LED 20a, only for a given time. The violet light V emitted from the V-LED 20a is used for the focusing of the observation target. After the elapse of the given time, again, the light source control unit 22 turns on all the V-LED 20a, the B-LED 20b, the G-LED 20c, and the R-LED 20d and emits the normal light or the special light.

As illustrated in FIG. 2, the illumination light emitted from the light source 20 enters a light guide 24 inserted into the insertion part 12a via a light path coupling part (not illustrated) formed with a mirror, a lens, or the like. The light guide 24 is built in the endoscope 12 and a universal cord, and propagates the illumination light up to the distal end part 12d of the endoscope 12. The universal cord is a cord that connects the endoscope 12, and the light source device 14 and the processor device 16 together. In addition, multimode fiber can be used as the light guide 24. As an example, a fine-diameter fiber cable of which the core diameter is 105 μm, the clad diameter is 125 μm, and a diameter including a protective layer used as an outer cover is ϕ0.3 mm to 0.5 mm can be used for the light guide 24.

The distal end part 12d of the endoscope 12 is provided with an illumination optical system 30a and an imaging optical system 30b. The illumination optical system 30a has an illumination lens 32. The observation target is illuminated with the illumination light propagated through the light guide 24 via the illumination lens 32. The imaging optical system 30b has an objective lens 34, a magnifying optical system 36, and an imaging sensor 38. Various kinds of light, such as reflected light from the observation target, scattered light, and fluorescence, enters the imaging sensor 38 via the objective lens 34 and the magnifying optical system 36. Accordingly, the image of the observation target is formed on the imaging sensor 38.

The magnifying optical system 36 comprises a zoom lens 36a that magnifies the observation target, and a lens drive unit 36b that moves the zoom lens 36a in an optical axis direction CL. The zoom lens 36a magnifies or reduces the observation target of which the image is formed on the imaging sensor 38 by freely moving between a telephoto end and a wide end in accordance with a zoom control performed by the lens drive unit 36b. Additionally, the zoom lens 36a is also used for focusing on the observation target illuminated with the normal light or the special light. The details of the focusing using the zoom lens 36a will be described below.

The imaging sensor 38 is a color imaging sensor that images the observation target irradiated with the illumination light. Each pixel of the imaging sensor 38 is provided with any one of a red (R) color filter, a green (G) color filter, and a blue (B) color filter. The imaging sensor 38 receives light in the range of from violet light to blue light with a B pixel provided with the B color filter, receives green light with a G pixel provided with the G color filter, and receives red light with an R pixel provided with the R color filter. Image signals of respective RGB colors are output from the respective color pixels. The imaging sensor 38 transmits the output image signals to a CDS/AGC circuit 40.

In the normal mode, the imaging sensor 38 images the observation target illuminated with the normal light, thereby outputting a Bc image signal from the B pixel, outputting a Gc image signal from the G pixel, and outputting an Rc image signal from the R pixel. Additionally, in the special mode, the imaging sensor 38 images the observation target illuminated with the special light, thereby outputting a Bs image signal from the B pixel, outputting a Gs image signal from the G pixel, and outputting an Rs image signal from the R pixel. Additionally, in the normal mode and the special mode, in a case where the observation target is illuminated with the violet light V during the zooming operation, the imaging sensor 38 images the observation target illuminated with the violet light V, thereby outputting a Bp image signal from the B pixel, outputting a Gp image signal from the G pixel, and outputting an Rp image signal from the R pixel.

As the imaging sensor 38, a charge coupled device (CCD) imaging sensor, a complementary metal-oxide semiconductor (CMOS) imaging sensor, or the like is available. Additionally, instead of the imaging sensor 38 provided with the color filters in the primary colors of RGB, a complementary color imaging sensor comprising complementary color filters in C (cyan), M (magenta), Y (yellow), and G (green) may be used. In a case where the complementary color imaging sensor is used, image signals of four colors of CMYG are output. For this reason, the same respective RGB image signals as those in the imaging sensor 38 can be obtained by converting the image signals of four colors of CMYG into image signals of three colors of RGB through color conversion between complementary colors and the primary colors. Additionally, instead of the imaging sensor 38, a monochrome sensor that is not provided with the color filters may be used.

The CDS/AGC circuit 40 performs correlated double sampling (CDS) and automatic gain control (AGC) on analog image signals received from the imaging sensor 38. An analog-to-digital (A/D) conversion circuit 42 converts the analog image signals, which have passed through the CDS/AGC circuit 40, into digital image signals. The A/D conversion circuit 42 inputs the digital image signals after the A/D conversion to the processor device 16.

The processor device 16 comprises an image signal acquisition unit 50, a digital signal processor (DSP) 52, a noise reduction unit 54, an image processing unit 58, a display control unit 60, and a zoom control processing unit 61. Hardware structures of respective units, such as the image signal acquisition unit 50, the noise reduction unit 54, the image processing unit 58, the display control unit 60, and the zoom control processing unit 61, are various processors as shown below. Various processors include exclusive electric circuits, which are processors having circuit configurations exclusively designed to execute specific processing, such as a central processing unit (CPU) that is a general-purpose processor that executes software (programs) to function as various processing units, a programmable logic device (PLD) that is a processor capable of changing a circuit configuration after manufacture of a field programmable gate array (FPGA) or the like, and an application specific integrated circuit (ASIC). In addition, the same applies the respective units inside the endoscope 12 and the light source device 14.

The image signal acquisition unit 50 (equivalent to the "image acquisition unit" of the invention) acquires digital image signals corresponding to the observation modes from the endoscope 12. In the case of the normal mode, the Bc image signal, the Gc image signal, and the Rc image signal are acquired as the normal image. In the case of the special mode, the Bs image signal, the Gs image signal, and the Rs image signal are acquired as the special image. In the normal mode and the special mode, in a case where the observation target is illuminated with the violet light V during the zooming operation, the Bp image signal, the Gp image signal, and the Rp image signal are acquired.

The DSP 52 performs various kinds of signal processing, such as defect correction processing, offset processing, gain correction processing, linear matrix processing, gamma conversion processing, demosaicing processing, and the like, on the image signals acquired by the image signal acquisition unit 50. In the defect correction processing, a signal of a defective pixel of the imaging sensor 38 is corrected. In the offset processing, a dark current component is removed from the image signals subjected to the defect correction processing, and an accurate zero level is set. In the gain correction processing, a signal level is adjusted by multiplying the image signals subjected to the offset processing by a specific gain.

The linear matrix processing enhances color reproducibility on the image signals subjected to the gain correction processing. In the gamma conversion processing, brightness and saturation of image signals subjected to the linear matrix processing are adjusted. By performing the demosaicing processing (also referred to as equalization processing or synchronization processing) on the image signals subjected to the gamma conversion processing, a signal of a color that runs short in each pixel is generated by interpolation. By means of this demosaicing processing, all pixels have signals of respective RGB colors. The noise reduction unit 54 performs noise reducing processing using, for example, a moving average method, a median filter method, or the like on the image signals subjected to the demosaicing processing or the like in the DSP 52, and reduces noise.

The image processing unit 58 comprises a normal image processing unit 62, a special image processing unit 64, and a focus-adjusting image generation unit 66. The normal image processing unit 62 operates in a case where the normal mode is set, and performs color conversion processing, color enhancement processing, and structure enhancement processing on the received normal image. In the color conversion processing, color conversion processing is performed on the RGB image signals by 3×3 matrix processing, gradation transformation processing, three-dimensional look-up table (LUT) processing, and the like.

The color enhancement processing is performed on the normal image subjected to the color conversion processing. The structure enhancement processing is the processing of enhancing the structure of the observation target, and is performed on the normal image after the color enhancement processing. As described above, since the normal image subjected to the various kinds of image processing and the like up to the structure enhancement processing is an image obtained on the basis of the illumination light for normal mode in which the violet light V, the blue light Bx, the green light and the red light R are emitted in a well-balanced manner, the normal image is a natural-tone image. The normal image is input to the display control unit 60 as it is in a case where the normal mode is set.

The special image processing unit 64 operates in a case where the special mode is set. In the special image processing unit 64, the color conversion processing, the color enhancement processing, and the structure enhancement processing is performed on the received special image. The processing contents of the color conversion processing, the color enhancement processing, and the structure enhancement processing are the same as those of the normal image processing unit 62. Since the special image is an image obtained on the basis of illumination light for special mode in which the violet light V with a high absorption coefficient of hemoglobin of blood vessels has a larger quantity of light emission than the blue light Bx, the green light and the red light R in the other colors, the resolution of a blood vessel structure is higher than that of the other structures. The special image is input to the display control unit 60 as it is in a case where the special mode is set.

The focus-adjusting image generation unit 66 operates during the zooming operation in the normal mode and the special mode. In the focus-adjusting image generation unit 66, a focus-adjusting image for adjusting a focus on the observation target is generated on the basis of the Bp image signal. The generated focus-adjusting image is input to the display control unit 60. The details of the focus-adjusting image generation unit 66 will be described below.

The display control unit 60 performs a display control for displaying an image on the monitor 18 from the image processing unit 58. In a case where the normal mode, the display control unit 60 performs the control of displaying the normal image on the monitor 18. In a case where the special mode is set, the display control unit 60 performs the control of displaying the special image on the monitor 18. Additionally, in the normal mode and the special mode, the display control unit 60 performs the control of displaying the focus-adjusting image on the monitor 18 under given conditions during the zooming operation.

Figure 6:
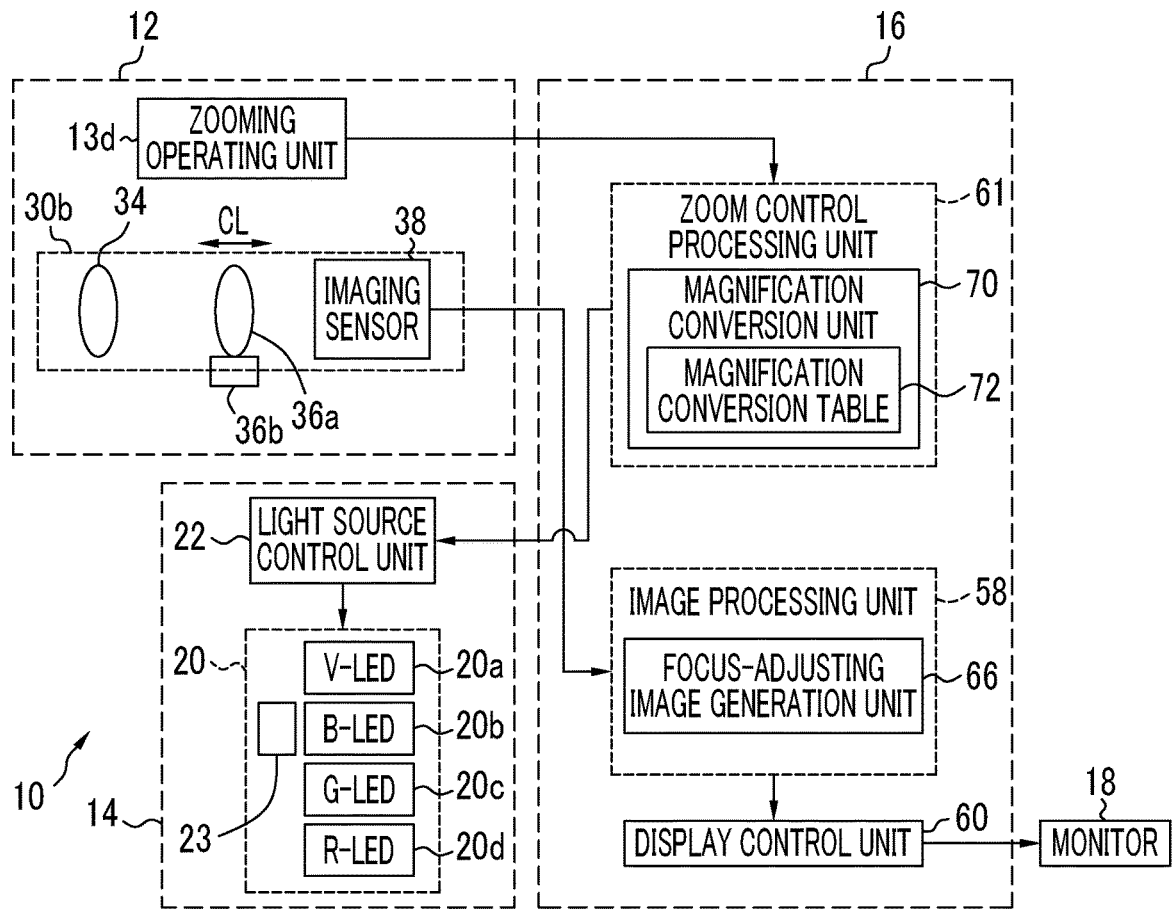
FIG. 6 is a block diagram illustrating a zoom control processing unit and the like of the first embodiment.

As illustrated in FIG. 6, the zoom control processing unit 61 controls the overall operation of the endoscope 12, the light source device 14, and the processor device 16 in a case where the operation of the zooming operating unit 13d is performed. The zoom control processing unit 61 instructs the light source control unit 22 to emit the violet light V (corresponding to the "short-wave light" of the invention) to in a case where the zooming operating unit 13d is operated. Accordingly, the observation target is illuminated with the violet light V. The imaging sensor 38 outputs the Bp image signal, the Gp image signal, and the Rp image signal by imaging the observation target illuminated with the violet light V.

Figures 7, 8:
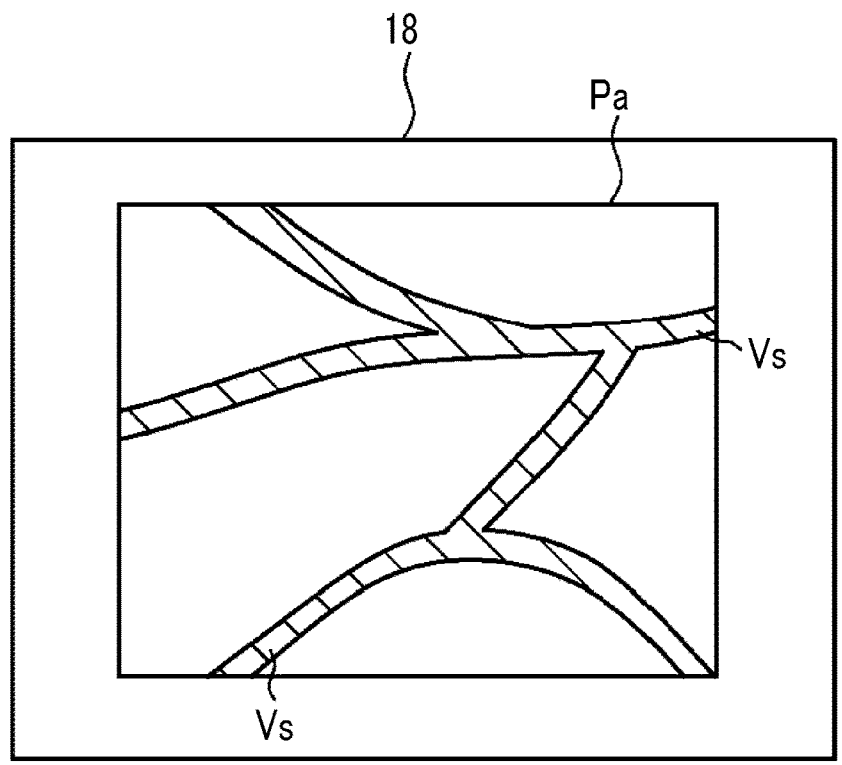
FIG. 7 is an image view illustrating a focus-adjusting image.
FIG. 8 is a table illustrating a magnification conversion table.

The focus-adjusting image generation unit 66 generates the focus-adjusting image (corresponding to a "first image" of the invention) on the basis of the Bp image signal among the image signals output from the imaging sensor 38. The generated focus-adjusting image is displayed on the monitor 18 by the display control unit 60. A user operates the zooming operating unit 13d such that the observation target has a target size, observing the focus-adjusting image. Here, as illustrated in FIG. 7, since a focus-adjusting image Pa is generated from the Bp image signal obtained by the violet light V of a wavelength range where the light absorption coefficient of hemoglobin of blood vessels is high, an edge structure, such as a blood vessel structure Vs, is displayed with high resolution. In addition, since the focus-adjusting image is a monochrome image, this focus-adjusting image may be displayed in parallel with the normal image acquired before the operation of the zooming operating unit 13d so that the focusing is easily performed. Additionally, with respect to the focus-adjusting monochrome image, a colored focus-adjusting image in which gradation balance is changed in a plurality of stages, for example, three stages, and images in the respective stages are allocated to each ch of RGB, respectively, may be displayed on the monitor 18.

On the focus-adjusting image, edges, such as the blood vessel structure, are blurred and displayed in a case where the observation target is not focused, while the edges are clearly displayed in a case where the observation target is in focus. Hence, the user operates the zooming operating unit 13d such that the edges in the focus-adjusting image are clearly displayed after the observation target is magnified to the target size. Then, in a case where the edges are clearly displayed and the zoom lens 36a is at a first lens position, the operation of the zooming operating unit 13d is stopped. In a case where the zooming operating unit 13d is not operated for a given time or more, the observation target is regarded as being focused, and the magnification of the zoom lens 36a in this case is transmitted to the zoom control processing unit 61 as a first magnification.

The zoom control processing unit 61 has a magnification conversion unit 70 for converting the first magnification of the zoom lens 36a focused on the observation target illuminated with the violet light V into a second magnification for providing a focus on the observation target illuminated with the normal light or the special light. The magnification conversion unit 70 performs the conversion from the first magnification into the second magnification, using a magnification conversion table 72. As illustrated in FIG. 8, the magnification conversion table 72 associates the first magnification with the second magnification for normal light for providing a focus on the observation target illuminated with the normal light, while magnifying the observation target to the same size as this first magnification. The table is saved in a recording medium referred to as a hard disk or a solid state drive (SSD) (not illustrated). Besides, the first magnification and the second magnification for special light for providing a focus on the observation target illuminated with the special light while magnifying the observation target to the same size as the first magnification are stored in association with each other in the magnification conversion table 72.

In addition, the reason why the second magnification for normal light is different from the second magnification for special light is that proportions including long-wave light, such as the red light R, are different from each other in the normal light and the special light, and due to the difference between the proportions of the long-wave light, a position where the observation target is in focus in a case where illumination is made with the normal light and a position where the observation target is focused are different from each other. Additionally, the magnification conversion table 72 may be provided for each region, such as the esophagus, the stomach, or the large intestine. In this case, it is preferable to manually set the type of region to observe or to set the type through automatic determination from an image, using a console or the like.

Additionally, the magnification conversion table 72 is created using, for example, a phantom obtained by simulating light-scattering coefficients within human being's tissue. As a table creation method in the case of using the phantom, first, the violet light V is illuminated to the phantom, the zoom lens 36*a* is moved, and focusing is performed on the observation target. A magnification in a case where the observation target is focused is defined as the first magnification. Next, the focusing of the observation target is performed by illuminating the phantom with the normal light. In that case, the zoom lens 36*a* is moved around the first magnification to perform the focusing. A magnification in a case where a focus is provided is defined as the second magnification for the normal image.

The first magnification and the second magnification for normal light are stored in association with each other in the magnification conversion table 72. A series of methods are performed by changing the magnification of the zoom lens 36*a*. Additionally, after the table in a case where illumination is performed with the normal light is created, a table is also created in the same methods for the special light. In addition to creating the table using the phantom, a table may be created by the simulation calculation based on modeling in which light-scattering coefficients within human being's tissue are expressed.

The magnification conversion unit 70 selects the second magnification corresponding to the first magnification of the zoom lens 36*a* with reference to a set observation mode and the magnification conversion table 72. For example, in a case where the magnification conversion table 72 illustrated in FIG. 8 is used and in a case where an observation mode is set to the normal mode and the first magnification is 10 times, the second magnification becomes 11 times in which the first magnification is multiplied by 1.1. Additionally, in a case where an observation mode is set to the special mode and the first magnification is 10 times, the second magnification becomes 12 times in which the first magnification is multiplied by 1.2.

The zoom control processing unit 61 provides an instruction to the lens drive unit 36*b* such that the magnification of the zoom lens 36*a* becomes the second magnification selected in the magnification conversion unit 70. Accordingly, the magnification of the zoom lens 36*a* is changed from the first magnification to the second magnification. The lens drive unit 36*b* is constituted of a well-known motor. Accordingly, the position of the zoom lens 36*a* moves from the first lens position to a second lens position. Additionally, the zoom control processing unit 61 instructs the light source control unit 22 to emit the illumination light corresponding to the observation mode. From the light source device 14 in accordance with this instruction, the observation target is illuminated with the normal light in the case of the normal mode, and the observation target is illuminated with the special light in the case of the special mode. Then, an image (corresponding to a "second image" of the invention) corresponding to the observation mode is obtained by performing the imaging of the observation target by the imaging sensor 38. The obtained image is displayed on the monitor 18. The image displayed on the monitor 18 is an image in which the observation target is substantially magnified to the target size and the observation target is focused.

Figure 9:
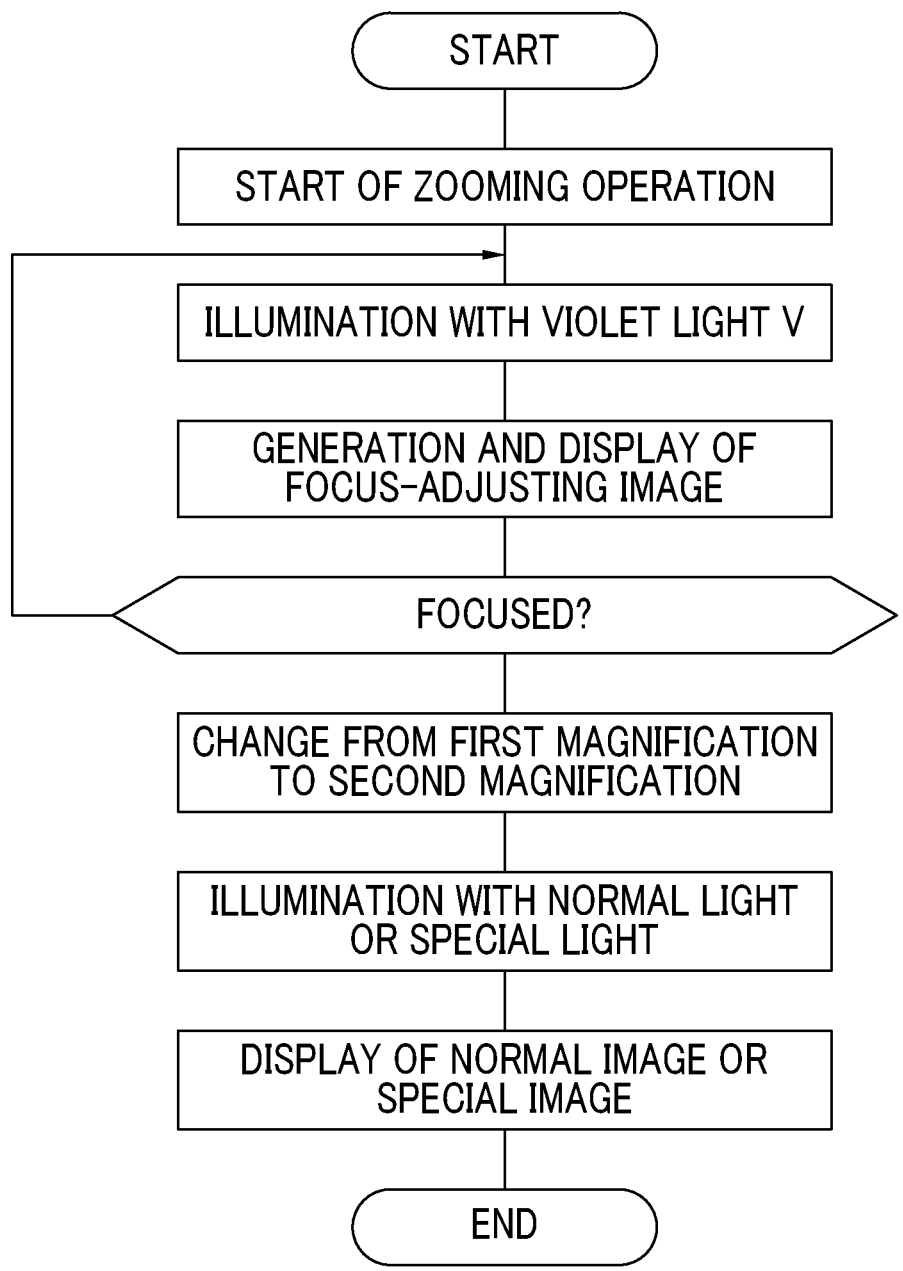
FIG. 9 is a flowchart illustrating a series of flows in which focusing is performed using a zoom lens, in the first embodiment.

Next, a series of flow in which the observation target is focused using the zoom lens will be described using a flowchart illustrated in FIG. 9. In a case where the normal mode or the special mode is set and in a case where the zooming operating unit 13*d* is operated, the light source control unit 22 drives the V-LED 20*a* to emit the violet light V. Accordingly, the observation target is illuminated with the violet light V, and the observation target illuminated with the violet light V is imaged by the imaging sensor 38 to obtain the Bp image signal, the Gp image signal, and the Rp image signal.

The focus-adjusting image generation unit 66 generates the focus-adjusting image on the basis of the Bp image signal. The focus-adjusting image is displayed on the monitor 18, and the user checks whether or not the observation target is focused viewing the focus-adjusting image. In that case, the user operates the zooming operating unit 13*d* to finely adjust the position of the zoom lens 36*a* such that the observation target is focused. Then, in a case where the user determines that the observation target is focused, the operation of the zooming operating unit 13*d* is stopped. The position of the zoom lens 36*a* in this case is set as the first lens position. After the operation of the zooming operating unit 13*d* is stopped and a given time has elapsed, the first magnification of the zoom lens 36*a* in a case where the operation of the zooming operating unit 13*d* is stopped is transmitted to the zoom control processing unit 61.

The magnification conversion unit 70 converts the first magnification of the zoom lens 36*a* into the second magnification for providing a focus on the observation target illuminated with the normal light or the special light. The zoom control processing unit 61 provides an instruction to the lens drive unit 36*b* such that the magnification of the zoom lens 36*a* is switched from the first magnification to the second magnification. Accordingly, the magnification of the zoom lens 36*a* is changed to the second magnification, and the position of the zoom lens 36*a* moves from the first lens position to the second lens position. Additionally, the zoom control processing unit 61 turns on all the B-LED 20*b*, the G-LED 20*c*, and the R-LED 20*d* in addition to V-LED 20*a*, and provides an instruction to the light source control unit 22 so as to emit the normal light or the special light. Accordingly, the normal image or the special image is obtained by illuminating the observation target with the normal light or the special light and imaging the observation target illuminated with the normal light or special light. The normal image or the special image is displayed on the monitor 18.

In addition, in the above embodiment, in order to generate the focus-adjusting image, the observation target is illuminated with the violet light V. However, the observation target may be illuminated with the blue light Bx instead of or in addition to the violet light V. Additionally, in the above embodiment, the observation target is illuminated all the four colors of light of the violet light V, the blue light Bx, the green light and the red light R, and the normal light or the special light of which only the quantity-of-light ratios are made different from each other is emitted. However, in addition to the normal light or the special light, multicolor light including at least long-wave light, such as the red light R, among the four colors of light may be emitted. In this case, in order to provide a focus on the observation target illuminated with the multicolor light, the first magnification and the second magnification for multicolor light are stored in association with each other in the magnification conversion table 72.

In addition, in the above embodiment, the light to illuminate the observation target is switched from the violet light V to the normal light or the special light after the zoom lens 36a is switched from the first lens position to the second lens position. However, as long as the observation target illuminated with the violet light V is focused, the light to illuminate the observation target may be switched from the violet light V to the normal light or the special light before the zoom lens 36a is switched from the first lens position to the second lens position.

Second Embodiment

In a second embodiment, the observation target is illuminated using a laser light source and a fluorescent body instead of the four-color LEDs 20a to 20d illustrated in the above first embodiment. In the following, only portions different from the first embodiment will be described, and description of substantially the same portions as those of the first embodiment will be omitted.

Figure 10:
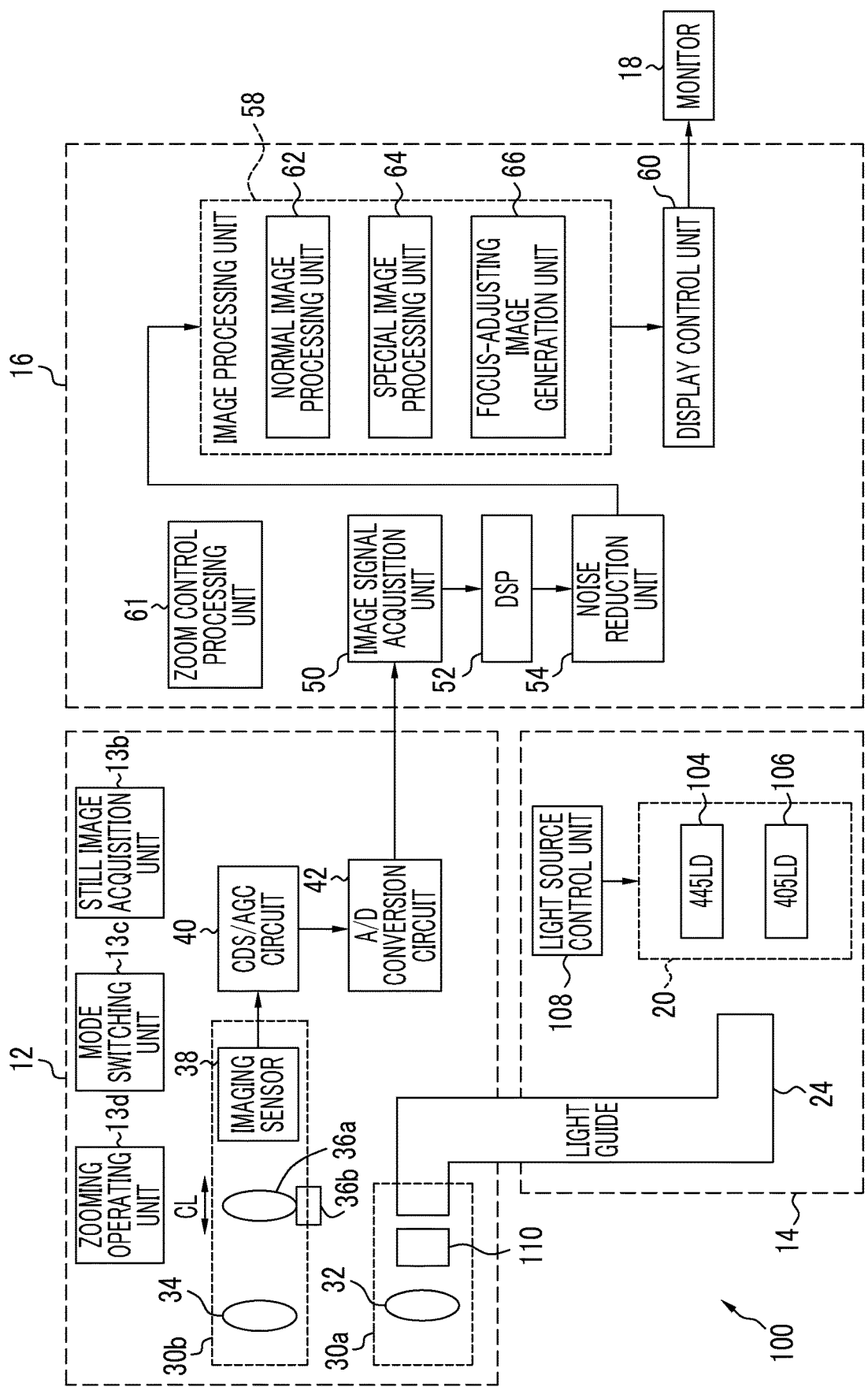
FIG. 10 is a block diagram illustrating the functions of an endoscope system of a second embodiment.

As illustrated in FIG. 10, in the endoscope system 100 of the second embodiment, in the light source 20 of the light source device 14, a blue laser light source that emits blue laser light having a central wavelength of 445±10 nm (written as "445LD"; LD represents Laser Diode) 104 and a blue-violet laser light source (written as "405LD") 106 that emits blue-violet laser light having a central wavelength of 405±10 nm are provided instead of the four-color LEDs 20a to 20d. The light emission from semiconductor light-emitting elements of the respective light sources 104 and 106 are individually controlled by a light source control unit 108, and the quantity-of-light ratio of the emitted light of the blue laser light source 104 and the emitted light of the blue-violet laser light source 106 is changeable.

The light source control unit 108 turns on the blue laser light source 104 in the case of the normal mode. In contrast, in the case of the special mode, both the blue laser light source 104 and the blue-violet laser light source 106 are turned on, and the light emission ratio of the blue laser light is controlled to become larger than the light emission ratio of the blue-violet laser light. Additionally, in the second embodiment, in the normal mode or the special mode, the light source control for the blue laser light source 104 and the blue-violet laser light source 106 is not changed even in a case where the zooming operating unit 13d is operated.

In addition, it is preferable that the half-width of the blue laser light or the blue-violet laser light is about ±10 nm. Additionally, as the blue laser light source 104 and the blue-violet laser light source 106, broad area type InGaN-based laser diodes can be utilized, and InGaNAs-based laser diodes and GaNAsb-based laser diodes can also be used.

Additionally a configuration using a light emitter, such as a light emitting diode, may be adopted as the above light source.

The illumination optical system 30a is provided with a fluorescent body 110 (wavelength converting member) that the blue laser light or the blue-violet laser light from the light guide 24 enters in addition to the illumination lens 32. The fluorescent body 110 is excited by the blue laser light to emit fluorescence. Additionally, a portion of the blue laser light is transmitted through the fluorescent body 110 without exciting the fluorescent body 110. The blue-violet laser light is transmitted through the fluorescent body 110 without exciting the fluorescent body 110. The inside of the body of the observation target is illuminated with the light emitted from the fluorescent body 110 via the illumination lens 32.

Figure 11:
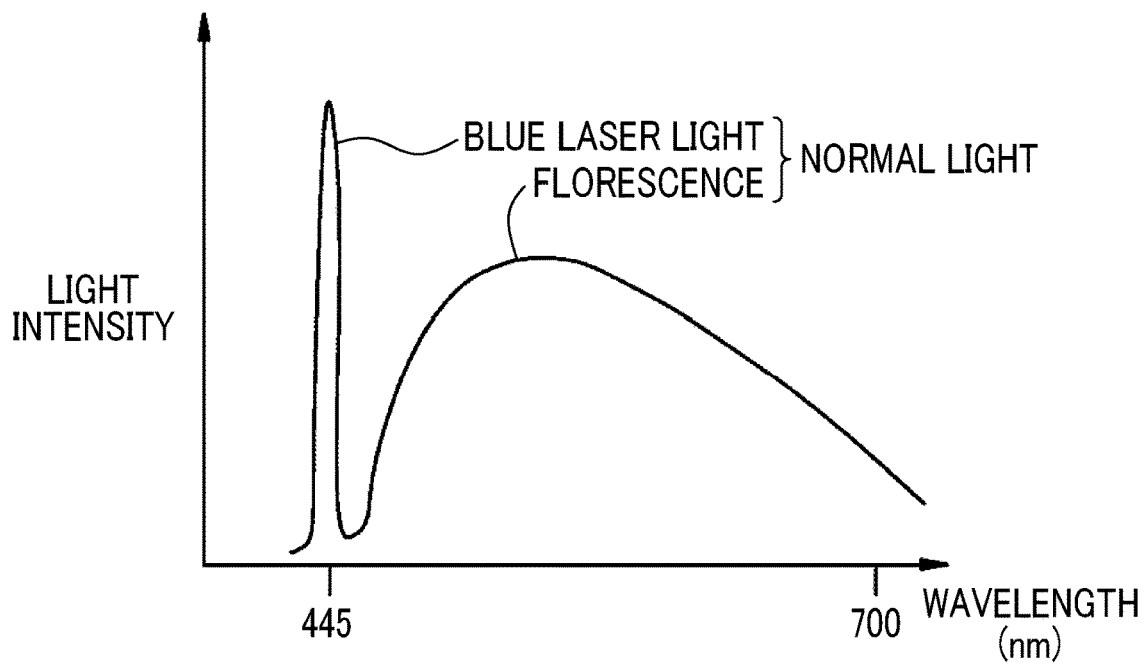
FIG. 11 is a graph illustrating the spectroscopic spectrum of normal light of the second embodiment.

Here, in the normal mode, mainly, the blue laser light enters the fluorescent body 110. Therefore, the broadband light for normal mode, which is obtained by combining the blue laser light (corresponding to "short-wave narrowband light" of the invention) with the fluorescence excited and emitted from the fluorescent body 110 due to the blue laser light as illustrated in FIG. 11, is illuminated to the observation target as the normal light. By imaging the observation target illuminated with the normal light by the imaging sensor 38, the normal image including the Bc image signal, the Gc image signal, and the Rc image signal is obtained. In addition, in the second embodiment, the "light source" of the invention corresponds to a configuration including the blue laser light source 104, the blue-violet laser light source 106, and the fluorescent body 110.

Figure 12:
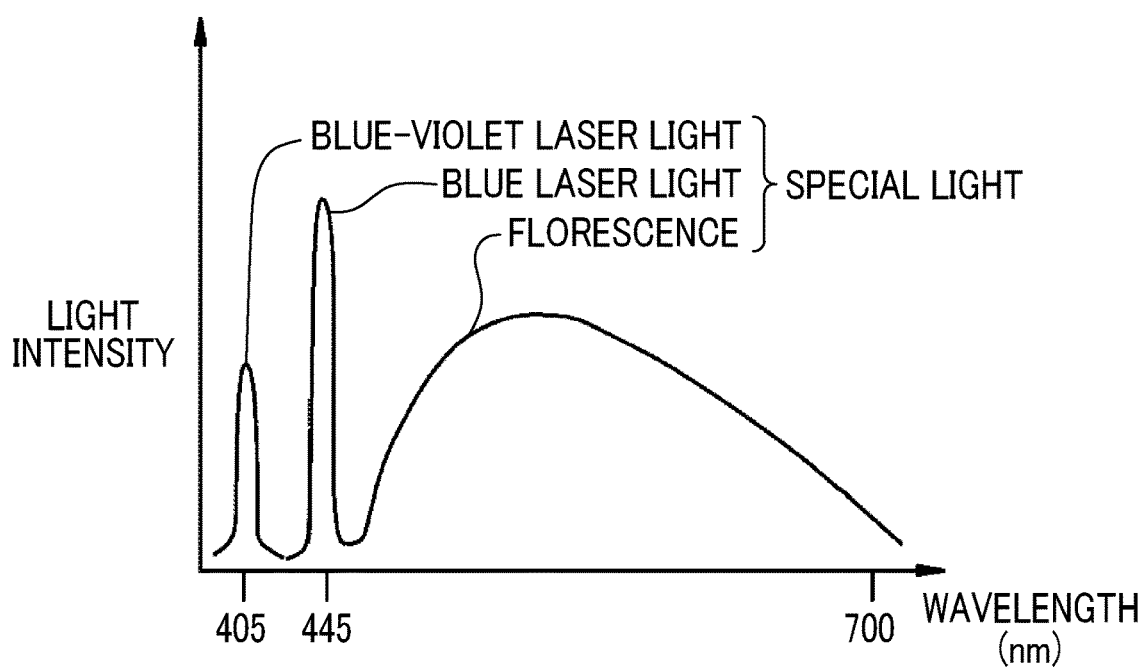
FIG. 12 is a graph illustrating the spectroscopic spectrum of special light of the second embodiment.

On the other hand, in the special mode, the blue-violet laser light (corresponding to "the short-wave narrowband light" of the invention) and the blue laser light enter the fluorescent body 110. Therefore, the broadband light for special mode, which is obtained by combining the blue-violet laser light, the blue laser light, and the fluorescence excited and emitted from the fluorescent body 110 due to the blue laser light together as illustrated in FIG. 12, is illuminated to the observation target as the special light. By imaging the observation target illuminated with the special light by the imaging sensor 38, the special image including the Bs image signal, the Gs image signal, and the Rs image signal is obtained.

In addition, as the fluorescent body 110, it is preferable to use those configured to include a plurality of types of fluorescent bodies (for example, a YAG-based fluorescent body or fluorescent bodies, such as BAM (BaMgAl$_{10}$O$_{17}$)) that absorb a portion of the blue laser light and are excited to emit light in green to yellow. As in the present configuration example, in a case where the semiconductor light-emitting elements are used as the excitation light sources of the fluorescent body 110 high-sensitive white light with a high emission ratio can be acquired, the intensity of the white light can be easily adjusted, and changes in color temperature and chromaticity of the white light can be suppressed to be small.

In addition, in a case where the spectra of the normal light and the special light are compared, respectively, the special light is light having a spectrum that has a peak (corresponding to "the first peak" of the invention) of the light intensity, such as a peak of the blue-violet laser light in the short-wave range, such as the blue range, and has a skirt in a longer wavelength side than the short-wave range, such as the fluorescence. On the other hand, the normal light is light having a spectrum that has a peak (corresponding to "the second peak" of the invention) of the light intensity, such as a peak of the blue laser light, in the short-wave range, such as the blue range, and has a peak on a longer wavelength side than the peak of the special light.

Figure 13:
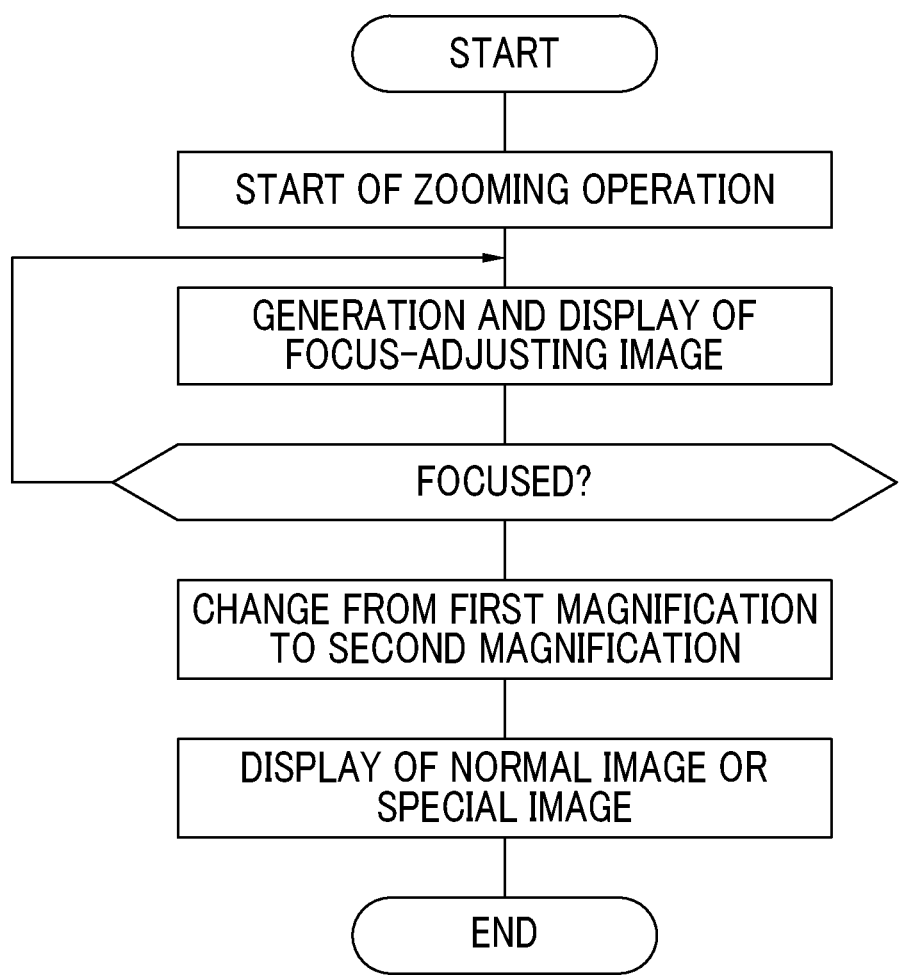
FIG. 13 is a flowchart illustrating a series of flows in which focusing is performed using a zoom lens, in the second embodiment.

In the second embodiment, since there is no change in the light source control even in a case where the zooming operating unit 13d is operated, a series of flows of performing focusing on the observation target using the zoom lens is different from that of the first embodiment. The series of flow in this second embodiment will be described using a flowchart illustrated in FIG. 13. In a case where the normal mode or the special mode is set and in a case where the zooming operating unit 13d is operated, the focus-adjusting image generation unit 66 generates the focus-adjusting image on the basis of the image signals having the wavelength information corresponding to the short-wave light among the image signals obtained in each mode. In the case where of the normal mode, the focus-adjusting image is generated on the basis of Bc image signal, and in the case of the special mode, the focus-adjusting image is generated on the basis of the Bs image signal.

The focus-adjusting image is displayed on the monitor 18, and the user performs the operation of the zooming operating unit 13*d* while viewing the focus-adjusting image. Then, in a case where the user determines that the observation target is focused, the operation of the zooming operating unit 13*d* is stopped. After the operation of the zooming operating unit 13*d* is stopped and a given time has elapsed, the first magnification of the zoom lens 36*a* in a case where the operation of the zooming operating unit 13*d* is stopped is transmitted to the zoom control processing unit 61.

The magnification conversion unit 70 converts the first magnification of the zoom lens 36*a* into the second magnification for providing a focus on the observation target illuminated with the normal light or the special light. The lens drive unit 36*b* changes the magnification of the zoom lens 36*a* from the first magnification to the second magnification. After the change to the second magnification, the observation target is illuminated with the normal light or the special light, and the observation target illuminated with the normal light or the special light is imaged. Accordingly, the normal image or the special image focused on the observation target is obtained. The normal image or the special image is displayed on the monitor 18.

Third Embodiment

In the third embodiment, the observation target is illuminated using a white light source, such as a xenon lamp, and the rotation filter instead of the four-color LEDs 20*a* to 20*d*. Additionally, the observation target may be imaged by a monochrome imaging sensor instead of the color imaging sensor 38. In the following, only portions different from the first embodiment will be described, and description of substantially the same portions as those of the first embodiment will be omitted.

Figure 14:
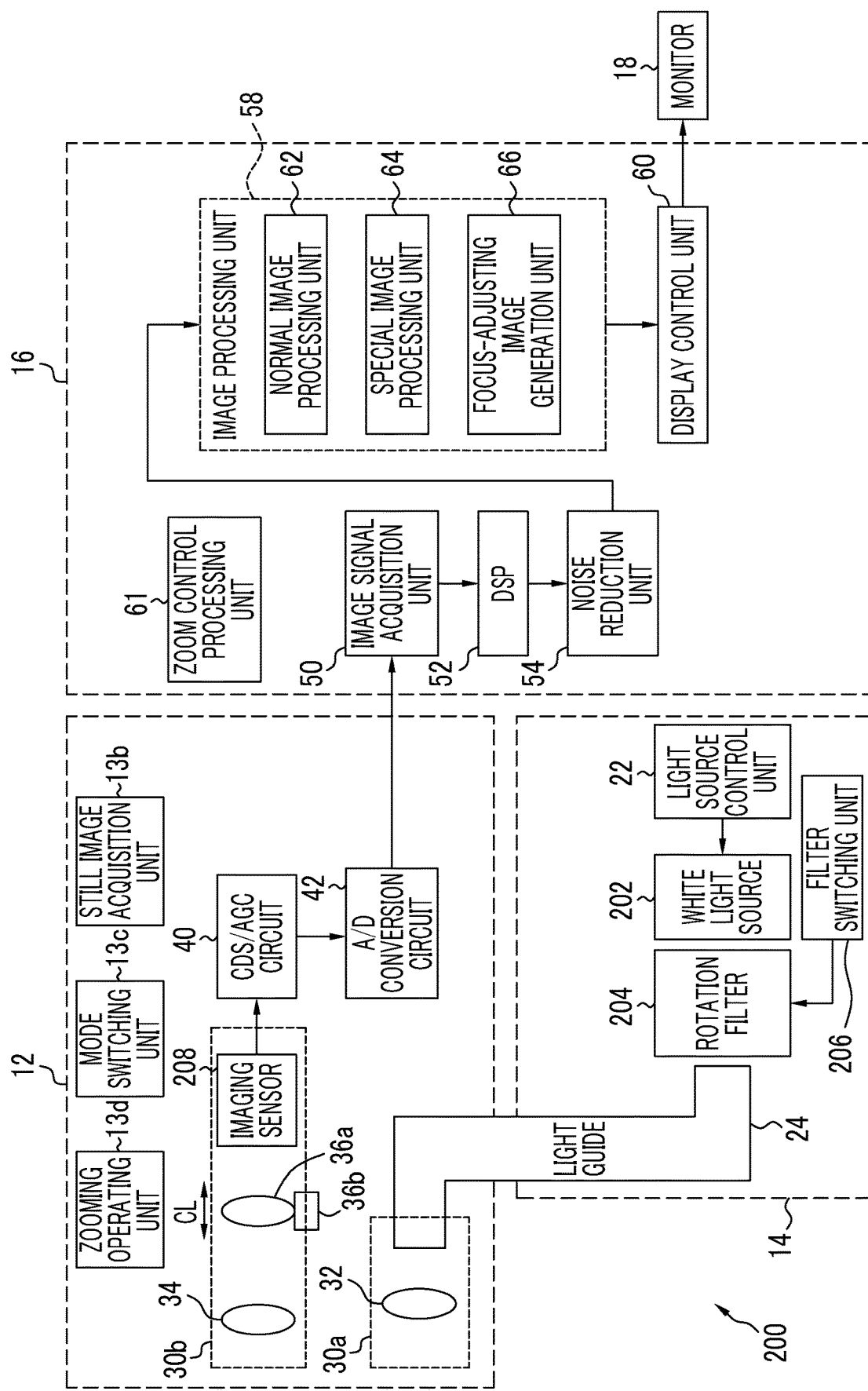
FIG. 14 is a block diagram illustrating the functions of an endoscope system of a third embodiment.

In an endoscope system 200 illustrated in FIG. 14, in the light source device 14, a white light source 202, a rotation filter 204, and a filter switching unit 206 are provided instead of the respective LEDs 20*a* to 20*d* of the endoscope system 10. Additionally, the imaging optical system 30*b* is provided with a monochrome imaging sensor 208, which is not provided with a color filter, instead of the color imaging sensor 38. In addition, in the third embodiment, the "light source" of the invention corresponds to a configuration including the white light source 202 and the rotation filter 204.

The white light source 202 is a xenon lamp, a white LED, or the like, and emits white light of which the wavelength range ranges from blue to red. The rotation filter 204 comprises a normal mode filter 210 that is provided on an inner side closest to a rotation axis thereof, and a special mode filter 212 provided outside the normal mode filter 210 (refer to FIG. 15).

The filter switching unit 206 moves the rotation filter 204 in a radial direction. Specifically, the filter switching unit 206 inserts the normal mode filter 210 into a white light path in a case where the normal mode is set by the mode switching unit 13*c*. Specifically, the filter switching unit 206 inserts the special mode filter 212 into the white light path in a case where the special mode is set by the mode switching unit 13*c*.

Figure 15:
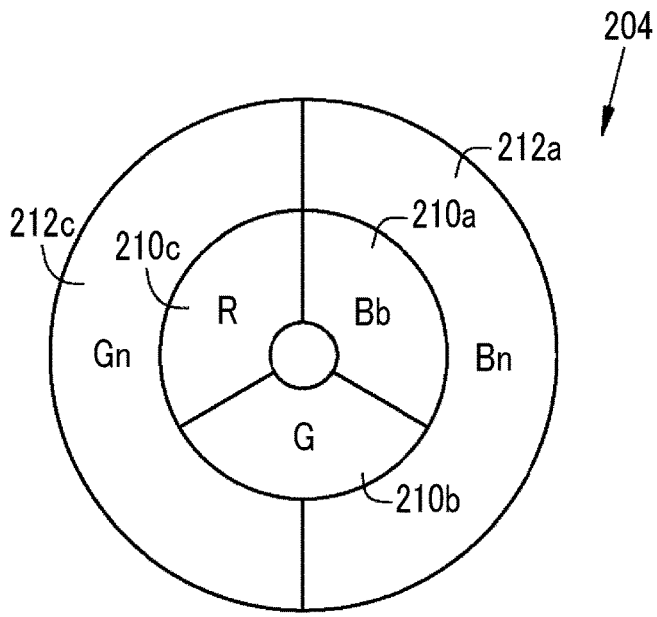
FIG. 15 is a plan view of a rotation filter.

As illustrated in FIG. 15, a Bb filter 210*a*, a G filter 210*b*, and an R filter 210*c* are provided in the circumferential direction in the normal mode filter 210. The Bb filter 210*a* transmits the broadband blue light Bb, which has a wavelength range of 400 to 500 nm, in the white light. The G filter 210*b* transmits the green light G in the white light. The R filter 210*c* transmits the red light R in the white light. Hence, in the normal mode, as the rotation filter 204 rotates, the broadband blue light Bb (corresponding to the "short-wave light" of the invention), the green light and the red light R (corresponding to the "long-wave light" of the invention) are sequentially radiated toward the observation target as the normal light. In addition, in the third embodiment, in the normal mode, the rotation filter 204 is similarly driven even in a case where the zooming operating unit 13*d* is operated. This same applies to the case of the special mode.

A Bn filter 212*a* and a Gn filter 212*b* are provided in the circumferential direction in the special mode filter 212. The Bn filter 212*a* transmits narrowband blue light Bn of 400 to 450 nm in the white light. The Gn filter 212*b* transmits narrowband green light Gn of 530 to 570 nm in the white light. Hence, in the special mode, as the rotation filter 204 rotates, the narrowband blue light (corresponding to the "short-wave light" of the invention), and the narrowband green light (corresponding to the "long-wave light" of the invention) are sequentially radiated toward the observation target as the special light.

In the endoscope system 200, in the normal mode, whenever the observation target is illuminated with the broadband blue light Bb, the green light and the red light R, the observation target is imaged by the monochrome imaging sensor 208. As a result, the Bc image signal is obtained at the time of the illumination with the broadband blue light Bb, the Gc image signal is obtained at the time of the illumination with the green light and the Rc image signal is obtained at the time of the illumination with the red light R. The normal image is constituted of the Bn image signal, the Gc image signal, and the Rc normal image.

In the special mode, the observation target is imaged by the monochrome imaging sensor 208 whenever the observation target is illuminated with narrowband blue light Bn and the narrowband green light Gn. Accordingly, the Bn image signal is obtained at the time of the illumination with the narrowband blue light Bn, and the Gn image signal is obtained at the time of the irradiation with the narrowband green light Gn. The special image is constituted of the Bn image signal and the Gn image signal.

In the third embodiment, since switching of the light to illuminate the observation target does not occur even in a case where the zooming operating unit 13*d* is operated, a series of flows of performing focusing on the observation target using the zoom lens is different from that of the first embodiment. Since the series of flows in the third embodiment is the same as that of the second embodiment, the description thereof will be omitted (refer to FIG. 13).

In addition, in the above first to third embodiments, the zoom lens that magnifies the observation target is used. However, in addition to this, the invention can be carried out as long as a movable lens that moves in an optical axis direction is provided. Additionally, in the above embodiments, by changing the magnification of the zoom lens 36*a* to the second magnification from the first magnification, the position of the zoom lens 36*a* is moved from the first lens position where the observation target illuminated with the violet light V is focused on the second lens position where the observation target y illuminated with the normal light or the special light is focused. However, the position of the zoom lens 36a may be changed by the other methods.

Figure 16:
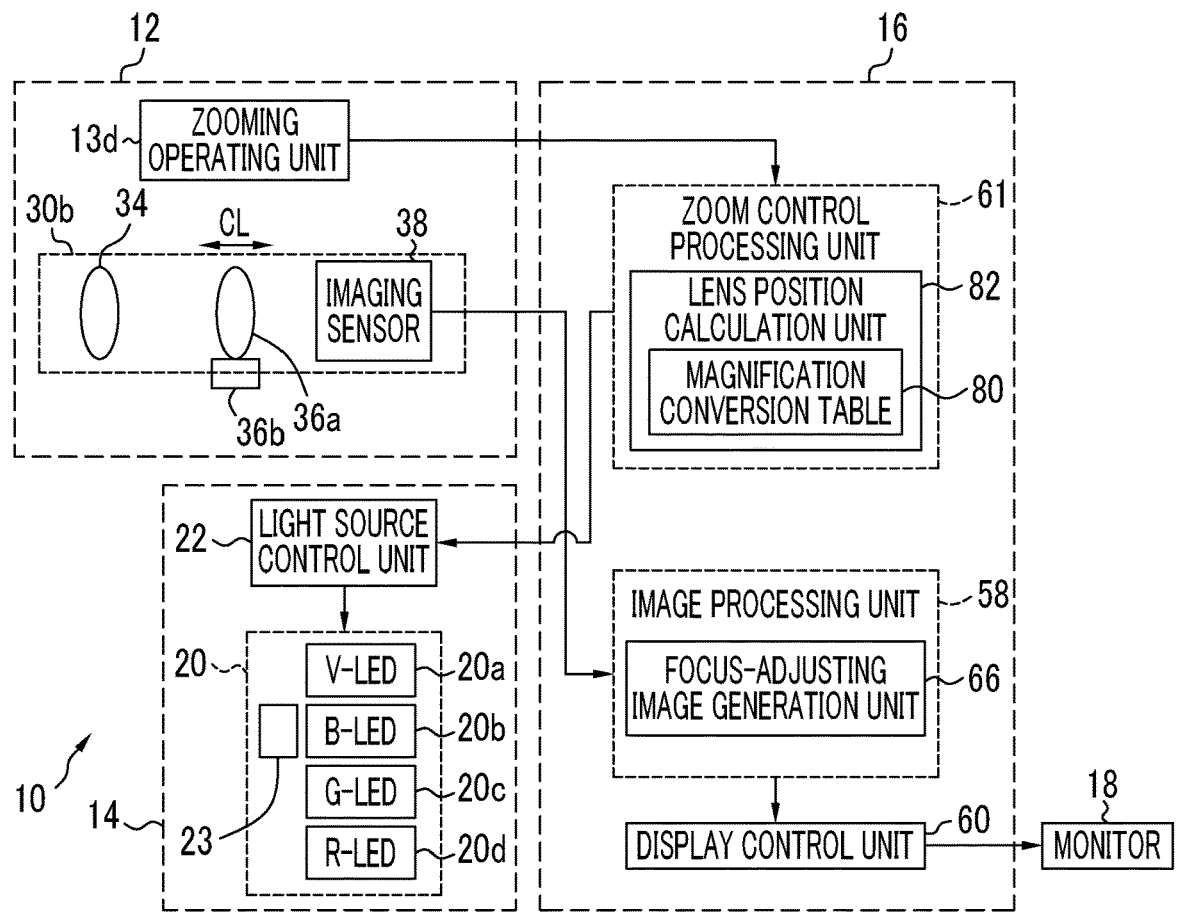
FIG. 16 is a block diagram illustrating a zoom control processing unit and the like in an embodiment different from the first embodiment.

For example, as illustrated in FIG. 16, a method of changing the position of the zoom lens 36a by providing the zoom control processing unit 61 with a position conversion table 80 where a relationship between the first lens position and the second lens position is stored in advance, and a lens position calculation unit 82, will be described below. First, the observation target illuminated with the violet light V is focused by the same method as those of the above embodiments, and the first lens position of the zoom lens 36a in a case where the focus is provided is transmitted to the lens position calculation unit 82. The lens position calculation unit 82 calculates the second lens position where the observation target illuminated with the normal light or the special light is focused from the first lens position with reference to the position conversion table 80. In a case where the second lens position is calculated, the lens drive unit 36b moves the position of the zoom lens 36a from the first lens position to the second lens position.

Additionally, in the above first to third embodiments, In a case where the normal image is displayed on the monitor 18 by the normal mode and in a case where the zooming operation is performed, switching to the special mode is temporarily made such that the special image is displayed as the focus-adjusting image on the monitor 18. In the special image, an edge structure, such as a blood vessel structure, is displayed with high resolution. Hence, the special image is also an image suitable for the focusing of the observation target. In addition, in a case where a focus is provided and the zooming operation is stopped, switching to the normal mode is made again such that the normal image is displayed on the monitor 18.

EXPLANATION OF REFERENCES

10: endoscope system
12: endoscope
12a: insertion part
12b: operating part
12c: bending part
12d distal end part
13a: angle knob
13b: still image acquisition unit
13c: mode switching unit
13d zooming operating unit
14: light source device
16: processor device
18: monitor
19: console
20: light source
20a: V-LED
20b: B-LED
20c: G-LED
20d: R-LED
22: light source control unit
23: wavelength cutoff filter
24: light guide
30a: illumination optical system
30b: imaging optical system
32: illumination lens
34: objective lens
36: magnifying optical system
36a: zoom lens
36b: lens drive unit
38: imaging sensor
40: CDS/AGC circuit
42: A/D conversion circuit
42: conversion circuit
50: image signal acquisition unit
52 DSP
54: noise reduction unit
58: image processing unit
60: display control unit
61: zoom control processing unit
62: normal image processing unit
64: special image processing unit
66: focus-adjusting image generation unit
70: magnification conversion unit
72: magnification conversion table
100: endoscope system
104: blue laser light source
106: blue-violet laser light source
108: light source control unit
110: fluorescent body
200: endoscope system
202: white light source
204: rotation filter
206: filter switching unit
208: imaging sensor
210: normal mode filter
210a: Bb filter
210b: G filter
210c: R filter
212: special mode filter
212a: Bn filter
212b: Gn filter

What is claimed is:

1. An endoscope system comprising:
a movable lens that moves in an optical axis direction;
a lens driver that moves the movable lens from a first lens position of the movable lens where an observation target illuminated with short-wave light is focused to a second lens position of the movable lens where the observation target illuminated with long-wave light having a longer wavelength than the short-wave light is focused,
wherein in a case where the movable lens is a zoom lens that magnifies the observation target, the endoscope system has a magnification conversion table in which a first magnification in a case where the zoom lens is at the first lens position and a second magnification in a case where the zoom lens is at the second lens position are stored in association with each other, wherein the first magnification and the second magnification magnify the observation target to a same size; and
a processor that converts the first magnification into the second magnification with reference to the magnification conversion table,
wherein the driver moves the zoom lens to the second lens position by setting the zoom lens to have the second magnification.

2. The endoscope system according to claim 1, further comprising:
a position conversion table in which a relationship between the first lens position and the second lens position is store,
wherein the processor further calculates the second lens position from the first lens position with reference to the position conversion table.

3. The endoscope system according to claim 2, further comprising:
a light source capable of independently emitting light of a plurality of colors including violet light, blue light, or red light,
wherein the short-wave light is the violet light or the blue light,
wherein the long-wave light is light including the red light among the light of the plurality of colors, and
wherein a first image obtained by imaging the observation target illuminated with the violet light or the blue light is displayed on a display.

4. The endoscope system according to claim 3, further comprising:
a light source controller that performs a control for emitting the short-wave light on the light source, and performs a control for switching the short-wave light to the long-wave light on the light source after the movable lens is moved from the first lens position to the second lens position.

5. The endoscope system according to claim 3, further comprising:
a light source controller that performs a control for emitting the short-wave light on the light source, and performs a control for switching the short-wave light to the long-wave light on the light source before the movable lens is moved from the first lens position to the second lens position.

6. The endoscope system according to claim 2,
wherein the short-wave light is light having a spectrum that has a first peak in a short-wave range and has a skirt on a longer wavelength side than the short-wave range, and
wherein the long-wave light is light that has a second peak on a longer wavelength side than the first peak, and
wherein a first image obtained by imaging the observation target illuminated with the short-wave light is displayed on a display.

7. The endoscope system according to claim 6, further comprising:
a light source capable of independently emitting light of a plurality of colors,
wherein the short-wave light or the long-wave light is multicolor light obtained by combining the light of the plurality of colors together.

8. The endoscope system according to claim 6,
wherein the short-wave light or the long-wave light is broadband light including one or a plurality of short-wave narrowband light rays and fluorescence obtained by converting wavelengths of the short-wave narrowband light rays using a wavelength converter.

9. The endoscope system according to claim 2,
wherein the processor further acquires a second image obtained by imaging the observation target illuminated with the long-wave light, and wherein the endoscope system further comprises:
a display that displays the second image.

10. The endoscope system according to claim 1, further comprising:
a light source capable of independently emitting light of a plurality of colors including violet light, blue light, or red light,
wherein the short-wave light is the violet light or the blue light,
wherein the long-wave light is light including the red light among the light of the plurality of colors, and
wherein a first image obtained by imaging the observation target illuminated with the violet light or the blue light is displayed on a display.

11. The endoscope system according to claim 10, further comprising:
a light source controller that performs a control for emitting the short-wave light on the light source, and performs a control for switching the short-wave light to the long-wave light on the light source after the movable lens is moved from the first lens position to the second lens position.

12. The endoscope system according to claim 10, further comprising:
a light source controller that performs a control for emitting the short-wave light on the light source, and performs a control for switching the short-wave light to the long-wave light on the light source before the movable lens is moved from the first lens position to the second lens position.

13. The endoscope system according to claim 10,
wherein the processor further acquires a second image obtained by imaging the observation target illuminated with the long-wave light, and wherein the endoscope system further comprises:
a display that displays the second image.

14. The endoscope system according to claim 1,
wherein the short-wave light is light having a spectrum that has a first peak in a short-wave range and has a skirt on a longer wavelength side than the short-wave range, and
wherein the long-wave light is light that has a second peak on a longer wavelength side than the first peak, and
wherein a first image obtained by imaging the observation target illuminated with the short-wave light is displayed on a display.

15. The endoscope system according to claim 14, further comprising:
a light source capable of independently emitting light of a plurality of colors,
wherein the short-wave light or the long-wave light is multicolor light obtained by combining the light of the plurality of colors together.

16. The endoscope system according to claim 14,
wherein the short-wave light or the long-wave light is broadband light including one or a plurality of short-wave narrowband light rays and fluorescence obtained by converting wavelengths of the short-wave narrowband light rays using a wavelength converter.

17. The endoscope system according to claim 1, further comprising:
a light source that emits broadband light having a wavelength range including the short-wave light and the long-wave light,
wherein the processor further acquires a first image having wavelength information corresponding to the short-wave light among images, in a plurality of bands, having information of the observation target illuminated with the broadband light; and
a display that displays the first image.

18. The endoscope system according to claim 1, further comprising:
a light source that sequentially emits the short-wave light and the long-wave light;
wherein the processor further acquires a first image obtained by imaging the observation target illuminated with the short-wave light; and
a display that displays the first image.

19. The endoscope system according to claim 1,
wherein the processor further acquires a second image obtained by imaging the observation target illuminated with the long-wave light, and wherein the endoscope system further comprises:
a display that displays the second image.

20. A method of operating an endoscope system having a movable lens that moves in an optical axis direction, the method comprising:
moving the movable lens, using a lens driver, from a first lens position of the movable lens where an observation target illuminated with short-wave light is focused to a second lens position of the movable lens where the observation target illuminated with long-wave light having a longer wavelength than the short-wave light is focused, wherein in a case where the movable lens is a zoom lens that magnifies the observation target, the endoscope system has a magnification conversion table in which a first magnification in a case where the zoom lens is at the first lens position and a second magnification in a case where the zoom lens is at the second lens position are stored in association with each other, wherein the first magnification and the second magnification magnify the observation target to a same size;
converting the first magnification into the second magnification with reference to the magnification conversion table; and
moving the zoom lens to the second lens position, using the lens driver, by setting the zoom lens to have the second magnification.

* * * * *